(12) United States Patent
Amminabavi et al.

(10) Patent No.: US 8,974,824 B2
(45) Date of Patent: Mar. 10, 2015

(54) LANTHANUM COMPOSITION

(75) Inventors: Nagaraj Amminabavi, Secunderabad (IN); Indu Bhushan, Secunderabad (IN); Satish Kumar Jain, Secunderabad (IN); Subhash Gore, Secunderabad (IN); Gnanadeva Chalapathy Gudipati, Secunderabad (IN); Balakrishnan Chinnu, Secunderabad (IN); Subramanian Iyer, Secunderabad (IN); Manoj P Kumar, Secunderabad (IN); Rajesh S Gupta, Secunderabad (IN)

(73) Assignee: Mylan Laboratories Ltd., Hyderabad (IN)

( * ) Notice: Subject to any disclaimer, the term of this patent is extended or adjusted under 35 U.S.C. 154(b) by 446 days.

(21) Appl. No.: 12/934,296

(22) PCT Filed: Mar. 24, 2009

(86) PCT No.: PCT/IN2009/000195
§ 371 (c)(1),
(2), (4) Date: Sep. 24, 2010

(87) PCT Pub. No.: WO2009/118760
PCT Pub. Date: Oct. 1, 2009

(65) Prior Publication Data
US 2011/0020456 A1    Jan. 27, 2011

(30) Foreign Application Priority Data

Mar. 26, 2008  (IN) .............................. 737/CHE/2008

(51) Int. Cl.
*A61K 9/14* (2006.01)
*A61K 33/24* (2006.01)
*A61K 9/20* (2006.01)

(52) U.S. Cl.
CPC ............... *A61K 33/24* (2013.01); *A61K 9/2013* (2013.01); *A61K 9/2054* (2013.01); *A61K 9/2077* (2013.01)
USPC ............ 424/464; 424/617; 424/715; 424/480

(58) Field of Classification Search
CPC ... A61K 33/24; A61K 9/2013; A61K 9/2054; A61K 9/2077
USPC .................................. 424/464, 617, 715, 480
See application file for complete search history.

(56) References Cited

U.S. PATENT DOCUMENTS

| 5,968,976 A | 10/1999 | Murrer et al. |
| 7,192,609 B2 | 3/2007 | Abrams et al. |
| 7,381,428 B2 | 6/2008 | Ferdinando et al. |
| 2005/0079135 A1 | 4/2005 | Haslam et al. |
| 2006/0198885 A1 * | 9/2006 | Dharmadhikari et al. .... 424/464 |
| 2007/0116782 A1 | 5/2007 | Abrams et al. |
| 2008/0160163 A1 * | 7/2008 | Schmidt et al. ................ 426/648 |
| 2008/0166406 A1 * | 7/2008 | Kristjansson ................. 424/465 |

FOREIGN PATENT DOCUMENTS

| EP | 1864677 A1 | 12/2007 |
| JP | 62145024 A | 6/1987 |

OTHER PUBLICATIONS

International Search Report, PCT/IN09/00195, mailed Oct. 13, 2009.

* cited by examiner

*Primary Examiner* — Mina Haghighatian (57) ABSTRACT

The present invention discloses stable, solid oral pharmaceutical composition comprising Lanthanum carbonate having more than 6 molecules of water per molecule of lanthanum carbonate and pharmaceutically acceptable carriers or diluents, wherein said carrier or diluent excludes monosaccharide/s or disaccharide/s, such that the composition has comparable in-vitro dissolution profile similar to that of FOSRENOL®.

Also disclosed is a wet granulation process for making the same.

14 Claims, 2 Drawing Sheets

Figure 1: Accelerated XRD Stability of Example 1

Figure 2: Accelerated XRD Stability of Example 4

Figure 3: Comparative dissolution study Example 7 Vs. Example 8

LANTHANUM COMPOSITION

FIELD OF INVENTION

The present invention relates to solid oral pharmaceutical composition containing Lanthanum carbonate and process to make the same.

BACKGROUND OF THE INVENTION AND RELATED PRIOR ART

Oral ingestion is one of the primary routes used for drug administration. This route provides a convenient method of effectively achieving both local and systemic effects. The properties of Lanthanum make it a good candidate as a phosphate binder. It has a high affinity for binding phosphorous and in the form of its carbonate salt, has a low solubility that limits gastrointestinal absorption. In the presence of HCl acid in the stomach, a proportion of administered Lanthanum carbonate is converted to the more highly soluble chloride salt with the release of carbon dioxide.

The commercially available composition of Lanthanum is a chewable tablet and is marketed under the brand name of FOSRENOL® in strengths of 500 mg, 750 mg and 1000 mg strengths.

FOSRENOL® inhibits absorption of phosphate by forming highly insoluble Lanthanum phosphate complexes, consequently reducing both serum phosphate and calcium phosphate product. In vitro studies have shown that in the physiologically relevant pH range of 3 to 5 in gastric fluid, Lanthanum binds approximately 97% of the available phosphate when Lanthanum is present in a two-fold molar excess to phosphate.

A stable pharmaceutical composition does not exhibit substantial decomposition of the active pharmaceutical ingredient during the time between the manufacture of the composition and its use by a patient. Lanthanum carbonate and a number of other drugs suffer from instability problems because the active pharmaceutical ingredient rapidly degrades in the presence of water or moisture. Lanthanum carbonate compositions tend to degrade, with formation of lanthanum hydroxycarbonate.

Palatability and "mouth feel" are extremely important factors in formulating high dose insoluble drugs, especially, if the composition is intended to be a chewable formulation. Insoluble materials usually have both an unpleasant mouth feel and an unpalatable taste due to chalkiness, grittiness, & dryness properties of these materials.

It is known that tablet blends may be dry mixed, dry-granulated or wet-granulated before tableting. The choice of the processing procedure viz., (dry mixing, dry granulation, wet granulation) depends on the properties of the drug and the chosen excipients. Generally, a dry manufacturing process is thought to be preferable for moisture-sensitive drugs.

JP 62-145024 discloses Lanthanum carbonate. Example 11 therein discloses $La_2(CO_3)_3H_2O$, i.e. the monohydrate.

U.S. Pat. No. 5,968,976 discloses pharmaceutical compositions for the treatment of hyperphosphataemia comprising Lanthanum carbonate hydrate where Lanthanum has three to six molecules of water. This document states that certain forms of Lanthanum carbonate exhibit improved performance i.e. higher phosphate removal, specifically Lanthanum carbonates having 3 to 6 molecules of water per molecule of Lanthanum carbonate, over then available standard commercial Lanthanum carbonate, which the inventors believed was the octahydrate form, and over $La_2(CO_3)_3H_2O$ i.e. monohydrate form or similar compounds.

U.S. Pat. No. 7,192,609 and US 2007/116782 disclose a method of preventing or treating urolithiasis i.e. kidney stones using nontoxic salts of rare earth metal ions e.g., Lanthanum salts, to bind dietary oxalate and preventing its absorption into the gastrointestinal tract. They also disclose that the hydration state of the Lanthanum salt is important; especially hydrates with waters of hydration of less than 7 moles water per mole of salt, and preferably the salts should contain 3 to 5 moles of water.

U.S. Pat. No. 7,381,428 discloses stabilized Lanthanum carbonate compositions, essentially prepared by dry mixing and compression of Lanthanum carbonate and stabilizers along with pharmaceutically acceptable additives, where monosaccharide or disaccharides are used as stabilizing agent to control/avoid the generation of hydroxycarbonate impurity in the composition.

U.S. application No: 2005/0079135 discloses chewable pharmaceutical compositions, containing Lanthanum carbonate having 3 to 8 molecules of water and the process of making pharmaceutical composition which involve dry mixing the ingredients and directly compressing the powder mixture or a slugging method or a roller compaction method.

These afore-mentioned prior art can be summarized as follows:
a) Lanthanum carbonate having a hydration between 3 to 6 water molecules is preferred;
b) Avoidance of water/wet granulation and a preference towards dry methods—compaction/direct compression is noticed;
c) Monosaccharide or disaccharide excipients are the preferred stabilizing agents to avoid/lower generation of hydroxycarbonate impurity.

There is a need in the art to provide stable and cost effective oral pharmaceutical composition comprising Lanthanum carbonate, where the composition is prepared utilizing alternative techniques and still prevents degradation of Lanthanum carbonate as current regulatory requirements preclude detectable decarboxylation for administration to patients.

The present invention is based on the finding that a stable, effective solid oral dosage form of Lanthanum carbonate can be prepared even with wet granulation technique and a high hydration state Lanthanum carbonate drug. Lanthanum carbonate used in the instant invention is in high hydration state, but still the composition prepared according the invention has comparable or higher in-vitro phosphate binding, as that of FOSRENOL®. The composition prepared according to the invention has a high load of Lanthanum carbonate, approximately more than 60% by weight of the composition, preferably between 65% to about 80% by weight of the composition. Also, a finer sized lanthanum carbonate is practically preferred for use in the composition. Drug particles having d (0.9) not more than 110 microns are preferred.

OBJECTS OF THE INVENTION

The present invention is related to a stable, solid oral composition comprising Lanthanum carbonate having more than six molecules of water per molecule of lanthanum carbonate, preferably eight molecules of water and a carrier or diluent wherein such diluent does not include a monosaccharide or a disaccharide, with a comparable or higher in vitro Phosphate binding capability to that of commercially available brand FOSRENOL®.

It is an object of the present invention is to provide a stable pharmaceutical composition of Lanthanum carbonate having more than six molecules of water per molecule of lanthanum carbonate—preferably eight molecules—and pharmaceutically acceptable diluents/carriers, prepared by wet granulation technique, wherein the composition is devoid of monosaccharide and/or disaccharides as stabilizers.

Another object of the present invention is to provide a stable pharmaceutical composition of Lanthanum carbonate preferably in octahydrate form, where the composition has high drug loading, preferably more than 65% by weight of the composition.

Another object of the present invention is to provide a stable pharmaceutical composition comprising Lanthanum carbonate, wherein the Lanthanum carbonate used has a particle size distribution such that d (0.9) is not more than 110 microns, preferably not more than 80 microns.

In one embodiment of the invention, the pharmaceutical composition is prepared by a process comprising:
(a) blending Lanthanum carbonate, at least one carrier or diluent and optionally other pharmaceutically acceptable excipients and granulating said mixture with a binder solution to form granulate;
(b) screening the granules and blending the granules with a lubricant; and
(c) compressing the blend of step [c] to form tablets.

In a preferred embodiment of the invention, a lanthanum carbonate composition is prepared by wet granulation process comprising the drug in its octahydrate form such that it constitutes more than 65% weight by weight of the composition, with a drug particle size such that d (0.9) is below 110 microns and a carrier/diluent wherein such diluent does not include a monosaccharide or a disaccharide.

In another embodiment, the invention relates to a method for treating hyperphosphatemia in a renal failure patient, controlling hyperparathyroidism in a patient with chronic renal insufficiency, controlling hyperparathyroidism in a patient with chronic renal insufficiency, comprising administering a composition prepared in accordance with the invention, described herein.

SUMMARY OF THE INVENTION

The invention provides stable Lanthanum carbonate compositions and methods for their preparation. In one aspect, the present invention provides a stable solid oral composition comprising: a) Lanthanum carbonate in high hydration state; b) at least one pharmaceutically acceptable carrier or diluent, wherein the carrier or diluent excludes a monosaccharide or a disaccharide and wherein the composition exhibits comparable or higher in vitro Phosphate binding capability to that of commercially available brand FOSRENOL®.

In a preferred embodiment of the invention, a lanthanum carbonate composition comprising the drug in its octahydrate form such that it constitutes more than 65% weight by weight of the composition, with a drug particle size such that d (0.9) is below 110 microns, preferably below 80 microns and a carrier/diluent wherein such diluent does not include a monosaccharide or a disaccharide. An additional aspect of the preferred embodiment envisages use of wet granulation technique for making the composition.

As presently contemplated, in one broad form, the invention provides a process to make a pharmaceutical formulation comprising the following steps:
(a) blending Lanthanum carbonate, at least one carrier or diluent [wherein the carrier or diluent is not a monosaccharide or a disaccharide] and optionally other pharmaceutically acceptable excipients and granulating the mixture with a binder solution to form granules;
(b) screening the granules and blending the granules with a lubricant, and
(c) compressing the blend of step [c] to form tablets.

Other aspect of the present invention includes use of this composition for the treatment of a disease or disorder in a subject in need thereof comprising administering to the subject a therapeutically effective amount of the compositions of the present invention.

Figure 1:
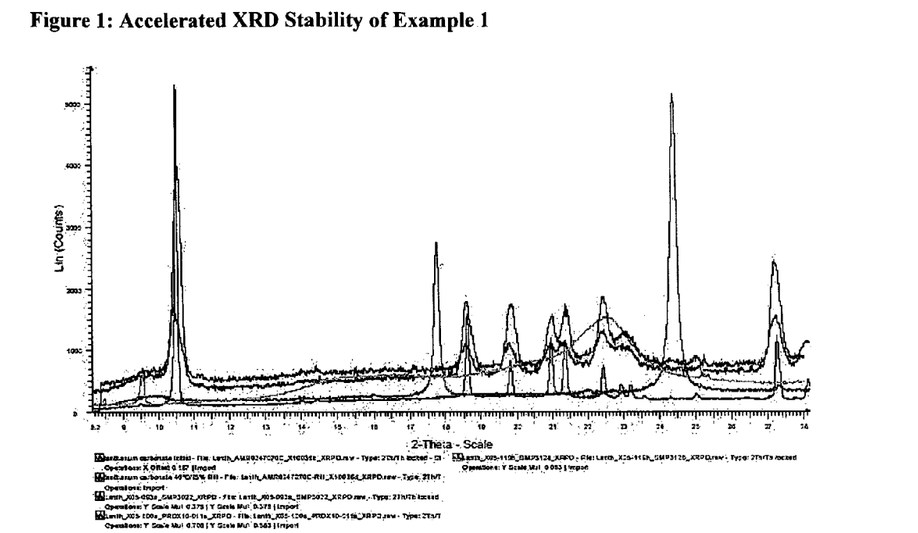
FIG. 1: Accelerated XRD Stability for composition of Example 1.
Figure 2:
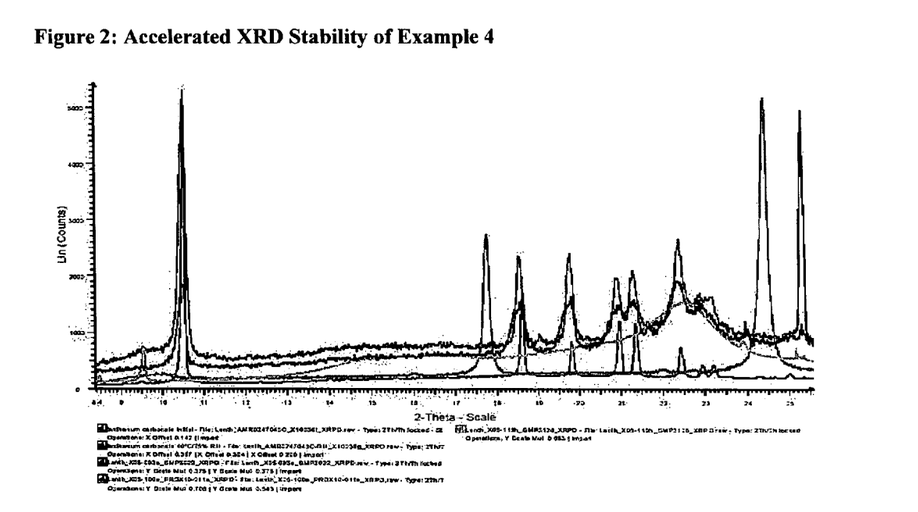
FIG. 2: Accelerated XRD Stability for composition of Example 4.
Figure 3:
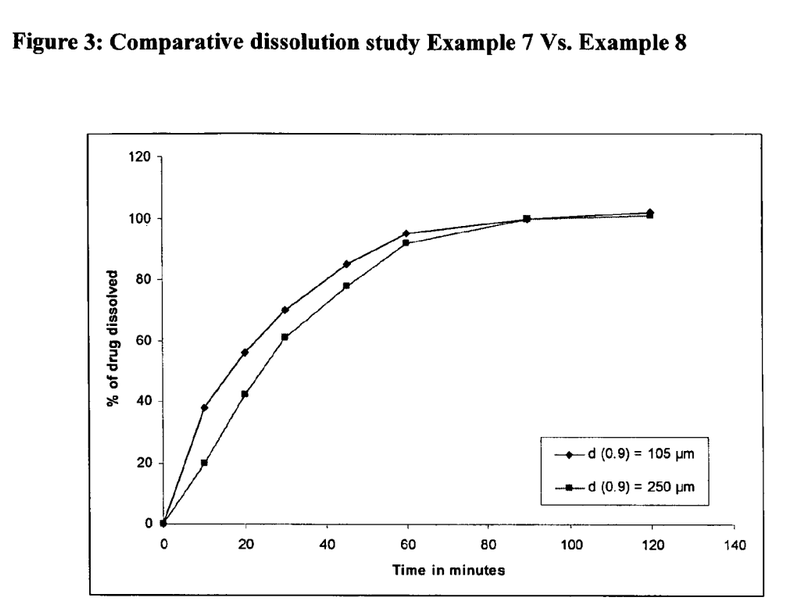
FIG. 3: Comparative dissolution for compositions of Example 7v/s Example 8.

GENERAL COMMENT FOR ALL THREE FIGURES

The XRD peaks depicted, alphabetically represent the following:
A—Hydroxycarbonate.
B—Lanthanum Carbonate
C—Lanthanum Carbonate chewable tablets, Initial sample
D—Lanthanum Carbonate chewable tablets, after three month at 40°/75% RH sample
E—Placebo
Comment for FIGS. 1 & 2:
The XRD data clearly revealed that lanthanum carbonate chewable tablet is stable and the decarboxylation of lanthanum carbonate was not seen over the entire length of experiment, even after storing the compositions at accelerated condition for the month.
Comment for FIG. 3:
The release profile obtained proves that the chewable tablets containing lanthanum carbonate having d (0.9) about 250 micron is comparatively dissolving slower than tablets containing lanthanum carbonate having d (0.9) not more than 105 micron.

Detailed Description Including Preferred Embodiments of the Invention

Generic drug manufactures constantly strive to create compositions that exhibit similar in-vitro and in-vivo profile as that of Innovator drug composition. The present inventors have now formulated a Lanthanum composition that contains Lanthanum Carbonate salt in high hydration state but still has comparable in-vitro phosphate binding capacity, to that of commercially available brand FOSRENOL® which contains Lanthanum Carbonate in low hydration state. The in-vitro phosphate binding have shown that the compositions of the present invention have equal or higher phosphate binding capacity to that of FOSRENOL®.

The present invention is directed to a formulation and a process for obtaining such composition. It should be noted that the hydration state of the Lanthanum compound present in the formulation of the present invention is relevant to the biological properties of the product as also the possibility of degradation of drug product to its hydroxycarbonate form. The prior art advises that for getting optimum phosphate binding, composition containing Lanthanum carbonate must have Lanthanum in preferably low hydration state.

In an effort to overcome the unpleasant mouth feel and an unpalatable taste due to chalkiness, grittiness & dryness properties of lanthanum carbonate, the inventors have employed Lanthanum carbonate having particle size d (0.9) not more than 110 microns, preferably not more than 80 microns. The particle size distribution of Lanthanum carbonate was determined by using Malvern analyzer.

The active agent in composition according to the invention is present in the amount of from 250-1000 mg e.g. 250 mg, 500 mg, 750 mg or 1000 mg. Approximately 2140 mg of Lanthanum carbonate octahydrate corresponds to 1000 mg of elemental lanthanum.

As used herein, a "stable composition" or "stabilized composition" or "stabilized lanthanum carbonate composition" refers to a composition containing lanthanum carbonate (of high hydration state) and one or more diluents or carriers excluding monosaccharides or disaccharides. The lanthanum carbonate in a stabilized lanthanum carbonate composition degrades into lanthanum hydroxycarbonate at a slower rate compared to lanthanum carbonate alone or not in the presence of other materials.

Lanthanum carbonate in high hydration state for the present invention means Lanthanum carbonate salt having more than six molecules of water, in between seven to ten, and preferably eight molecules of water i.e. octahydrate form of Lanthanum carbonate.

The composition may further comprise pharmaceutically acceptable additives known in the art. The term 'pharmaceutically acceptable additive' includes 'pharmaceutically acceptable excipient' within its ambit and the singular term includes plural as well. The pharmaceutically acceptable excipients may be one or more of diluents, binders, surfactants, lubricants, glidants, amino acids, sweetening agents, coloring agents and flavoring agent, such that no monosaccharide or disaccharides are used in the composition.

The term "diluent" or "carrier" as used herein is intended to mean inert substances used as carriers to create the desired bulk, flow properties, and compression characteristics in the preparation of tablets and capsules, excluding monosaccharide and disaccharide based excipients or stabilizers. Acceptable carriers or diluents include, but are not limited to, amino acids, Avicel pH 102, calcium carbonate, calcium phosphate-dibasic, calcium phosphate-tribasic, calcium sulfate, mannitol, microcrystalline cellulose, silicified microcrystalline cellulose, powdered cellulose, and the like can be used. The pharmaceutically inert diluent may be used in an amount of about 15% to about 25% by weight of the total weight of the dosage form.

The term "binder/granulating agent" is intended to mean substances used to cause adhesion of powder particles in tablet granulations. Suitable binders according to the present invention can be selected from, alkyl celluloses such as methyl cellulose, ethyl cellulose, hydroxyalkyl celluloses such as hydroxypropyl cellulose, low substituted hydroxypropyl cellulose, hydroxypropyl methylcellulose, sodium carboxymethyl cellulose, microcrystalline cellulose, gelatin, polyvinylpyrrolidone and eudragits.

Examples of suitable granulating fluids employed in the preparation of present composition include water, methylene chloride, isopropyl alcohol, acetone, methanol, ethanol and the like. The preferred granulating fluid is water.

Glidants improve the flowability of the powder making up the tablet during production. Glidants can be selected from selected from the group consisting of: silicon dioxide, colloidal silicon dioxide, fumed silicon dioxide, sodium aluminosilicate, calcium silicate, powdered cellulose, microcrystalline cellulose, corn starch, sodium benzoate, calcium carbonate, magnesium carbonate, asbestos free talc, metallic stearates, calcium stearate, magnesium stearate, zinc stearate, Stearowet C, magnesium lauryl sulfate, or magnesium oxide, where colloidal silicon dioxide is the preferred glidant.

The term "lubricant" as used herein is intended to mean substances used in tablet formulations to reduce friction during tablet compression. Suitable lubricants according to the present invention can be selected from calcium stearate, magnesium stearate, sodium lauryl sulfate, talc, mineral oil, stearic acid, zinc stearate, colloidal silicon dioxide, glyceryl behenate, polyethylene glycol, sodium stearyl fumarate, hydrogenated cottonseed oil, sodium benzoate, leucine or combinations thereof and other such materials known to those of ordinary person skilled in the art.

Amino acids include one or more compounds selected from alanine, arginine, aspartic acid, asparagine, cysteine, glutamic acid, glutamine, glycine, histidine, isoleucine, leucine, lysine, methionine, phenylalanine, proline, serine, threonine, tryptophan, tyrosine and valine; preferably glycine and lysine.

Sweetening agents may be selected from a wide range of materials such as water-soluble sweetening agents, water-soluble artificial sweeteners, and dipeptide based sweeteners, including mixtures thereof. Specific examples of sweeteners that can be included but are not limited to are Acesulfame potassium, calcium saccharinate, ammonium cyclamate, ammonium glycirhizinate, aspartame (N-L-α-aspartyl-L-phenylalanine 1-methylester).

The amount of each type of additive employed, e.g. carrier or diluent, binder, glidant and lubricant may vary within ranges known to be conventional in the art.

In a preferred embodiment, there is provided a process to make a pharmaceutical formulation comprising the following steps:
(a) blending Lanthanum carbonate, at least one carrier or diluent and optionally other pharmaceutically acceptable excipients and granulating said mixture with a binder solution to form granules,
(b) screening the granules of step [a] and blending them with magnesium stearate, and
(c) compressing the blend of step [b] to form tablets.

The compression of granules to tablets is carried out in a conventional manner.

The pharmaceutical composition of the present invention is stable; having comparable in vitro Phosphate binding capability to that of commercially available brand FOSRENOL®. The invention also contemplates reducing the amount of lanthanum hydroxycarbonate impurity generated, especially under formulation and extended storage conditions. There is, therefore, a concomitant reduction in unit cost, as the composition is prepared by inexpensive wet granulation technique, generation of low impurity and the composition possess comparable in vitro Phosphate binding capability to that of FOSRENOL®.

The following examples are intended to illustrate the benefits of the present invention, but not exemplify the full scope of the invention.

EXAMPLE 1

| Sr. No | Ingredients | mg/Tablets |
|---|---|---|
| 1 | Lanthanum carbonate | 2166.3 |
| 2 | Glycine | 53.0 |
| 3 | Avicel CE 15 | 71.0 |
| 4 | Hydroxypropyl cellulose | 64.0 |
| 5 | Acesulfame K | 31.0 |
| 6 | Prosolv SMCC 90 | 53.0 |
| 7 | Microcrystalline Cellulose | 424.0 |
| 8 | Sodium CMC | 42.0 |

-continued

| Sr. No | Ingredients | mg/Tablets |
|---|---|---|
| 9 | Powdered Cellulose | 298.0 |
| 10 | Colloidal Silicon dioxide | 23.0 |
| 11 | Talc | 17.0 |
| 12 | Magnesium Stearate | 17.0 |
| 13 | Purified Water | qs |
| | Tablet weight | 3259.0 |

Manufacturing Process:
1. All the ingredients were shifted through mechanical sifter fitted with suitable mesh size.
2. Ingredients like Lanthanum carbonate, glycine. Avicel CE 15, Acesulfame K, prosolve, and Sodium CMC were loaded in to the Rapid mixture granulator and dry mixed for 10 minute under Impeller slow speed and chopper off.
3. Binder solution was prepared by dissolving HPC in purified water under continues stirring to get clear solution.
4. Step 2 was granulated using the binder solution of step 3 in to the Rapid mixture granulator for 10 minute under Impeller slow speed and chopper off.
5. Wet granules were dried to achieved required LOD and milled using Quadra-co mill fitted with suitable mesh size
6. Granules of Step 5 were blended with the Talc, colloidal silicon dioxide, magnesium stearate and microcrystalline cellulose in bin blender for the period of 10 minutes.
7. Lubricated blend of step 6 was compressed using suitable tooling.

EXAMPLE 2

| Sr. No | Ingredients | mg/Tablets |
|---|---|---|
| 1 | Lanthanum carbonate | 2166.3 |
| 2 | Avicel CE 15 | 88.67 |
| 3 | Hydroxypropyl cellulose | 30.0 |
| 4 | Acesulfame K | 30.0 |
| 5 | Microcrystalline Cellulose (Part I) | 173.208 |
| 6 | Microcrystalline Cellulose (Part II) | 259.812 |
| 7 | Colloidal Silicon dioxide | 32.01 |
| 8 | Magnesium Stearate | 20.0 |
| 9 | Purified Water | qs |
| | Tablet weight | 2800.00 |

Manufacturing Process:
1. All the ingredients were shifted through mechanical sifter fitted with suitable mesh size.
2. Ingredients like Lanthanum carbonate, Avicel CE 15, Acesulfame K, colloidal silicon dioxide and Microcrystalline cellulose (Part I) were loaded in to the Rapid mixture granulator and dry mixed for 10 minute under Impeller slow speed and chopper off.
3. Binder solution was prepared by dissolving HPC in purified water under continues stirring to get clear solution.
4. Step 2 was granulated using the binder solution of step 3 in to the Rapid mixture granulator for 10 minute under Impeller slow speed and chopper slow.
5. Wet granules were dried to achieved required LOD and milled using Quadra-co mill fitted with suitable mesh size
6. Granules of Step 5 were blended with the magnesium stearate and microcrystalline cellulose (Part II) in bin blender for the period of 10 minutes.
7. Lubricated blend of step 6 was compressed using suitable tooling.

EXAMPLE 3

| Sr. No | Ingredients | mg/Tablets |
|---|---|---|
| 1 | Lanthanum carbonate | 2166.3 |
| 2 | Glycine | 66.67 |
| 3 | Avicel CE 15 | 88.67 |
| 4 | Hydroxypropyl cellulose | 30.0 |
| 5 | Acesulfame K | 30.0 |
| 6 | Colloidal Silicon dioxide | 32.01 |
| 7 | Microcrystalline Cellulose | 366.35 |
| 8 | Magnesium Stearate | 20.0 |
| 9 | Purified Water | qs |
| | Tablet weight | 2800.00 |

Manufacturing Process:
1. All the ingredients were shifted through mechanical sifter fitted with suitable mesh size.
2. Ingredients like Lanthanum carbonate, glycine. Avicel CE 15, Acesulfame K, colloidal silicon dioxide, and microcrystalline cellulose were loaded in to the Rapid mixture granulator and dry mixed for 10 minute under Impeller slow speed and chopper off.
3. Binder solution was prepared by dissolving HPC in purified water under continues stirring to get clear solution.
4. Step 2 was granulated using the binder solution of step 3 in to the Rapid mixture granulator for 10 minute under Impeller slow speed and chopper off
5. Wet granules were dried to achieved required LOD and milled using Quadra-co mill fitted with suitable mesh size
6. Granules of Step 5 were blended with the magnesium stearate in bin blender for the period of 10 minutes.
7. Lubricated blend of step 6 was compressed using suitable tooling.

EXAMPLE 4

| Sr. No | Ingredients | mg/Tablets |
|---|---|---|
| 1 | Lanthanum carbonate | 2140.037 |
| 2 | Avicel CE 15 | 88.67 |
| 3 | Hydroxypropyl cellulose | 42.0 |
| 4 | Acesulfame K | 30.0 |
| 5 | Colloidal Silicon dioxide | 32.0 |
| 6 | Microcrystalline Cellulose (Part I) | 122.0 |
| 7 | Microcrystalline Cellulose (Part II) | 325.0 |
| 8 | Magnesium Stearate | 20.0 |
| 9 | Purified Water | qs |
| | Tablet weight | 2799.70 |

Manufacturing Process:
1. All the ingredients were shifted through mechanical sifter fitted with suitable mesh size.
2. Ingredients like Lanthanum carbonate, Avicel CE 15, Acesulfame K, colloidal silicon dioxide and Microcrystalline cellulose (Part I) were loaded in to the Rapid mixture granulator and dry mixed for 10 minute under Impeller slow speed and chopper off.

3. Binder solution was prepared by dissolving HPC in purified water under continues stirring to get clear solution.
4. Step 2 was granulated using the binder solution of step 3 in to the Rapid mixture granulator for 10 minute under Impeller slow speed and chopper slow.
5. Wet granules were dried to achieved required LOD and milled using Quadra-co mill fitted with suitable mesh size
6. Granules of Step 5 were blended with the magnesium stearate and microcrystalline cellulose (Part II) in bin blender for the period of 10 minutes.
7. Lubricated blend of step 6 was compressed using suitable tooling.

EXAMPLE 5

| Sr. No | Ingredients | Unit weight (mg) 1000 mg |
|---|---|---|
| | Intragranular | |
| 1 | Lanthanum carbonate Octahydrate | 2166.30 |
| 2 | Glycine | 53.00 |
| 3 | Avicel CE 15 | 71.00 |
| 4 | HPC-EXF | 64.00 |
| 5 | Sucralose | 1.53 |
| 6 | Acesulfame Potassium | 31.00 |
| 7 | Ammoniated Glycyrrhizia | 0.13 |
| 8 | Powdered Cellulose | 151.10 |
| 9 | Sodium Carboxy Methyl Cellulose | 42.00 |
| 10 | Prosolv SMCC 90** | 53.00 |
| 11 | Aerosil pharma 200 P | 26.00 |
| 12 | Stearic Acid | 180.00 |
| | Extragranular | |
| 13 | Magnesium Stearate | 18.00 |
| 14 | Avicel pH 102 | 309.00 |
| 15 | Talc | 18.00 |
| | Total weight of tablet | 3184.00 |

Manufacturing Procedure:
1. Lanthanum carbonate octahydrate was mixed with Intragranular excipients and sifted through sifter fitted with screen #30,
2. Blend of Step 1 was loaded in to RMG and mixed for 10 minutes.
3. Preparation of binder solution: Hydroxypropyl cellulose is added to purified water under continues stirring to get clear solution
4. The Step-2 is granulated using binder solution of step-3 in RMG to get required wet mass of powder blend
5. The wet mass of step 4 was sifted through sifter fitted with screen #16,
6. Wet granules are dried for sufficient period time to get LOD between 2 to 4% at 60° C.
7. Dried granules of step-6 is sifted through sifter fitted with screen #20,
8. The granules blend of Step-7 was blended with the extragranular ingredients in bin blender for 10 minutes.
9. Blend of step-8 is compressed using 24 mm round punches and corresponding dies.

EXAMPLE 6

| Sr. No | Ingredients | Unit weight (mg) 1000 mg |
|---|---|---|
| | Intragranular | |
| 1 | Lanthanum carbonate Octahydrate | 2166.30 |
| 2 | Glycine | 53.00 |
| 3 | Avicel CE 15 | 71.00 |
| 4 | HPC-EXF | 100.00 |
| 5 | Sucralose | 1.53 |
| 6 | Acesulfame Potassium | 31.00 |
| 7 | Ammoniated Glycyrrhizia | 0.13 |
| 8 | Powdered Cellulose | 170.00 |
| 9 | Sodium Carboxy Methyl Cellulose | 42.00 |
| 10 | Prosolv SMCC 90** | 53.00 |
| 11 | Aerosil pharma 200 P | 26.00 |
| | Extragranular | |
| 12 | Magnesium Stearate | 20.00 |
| 13 | Avicel pH 102 | 430.00 |
| 14 | Talc | 20.00 |
| | Total weight of tablet | 3184.96 |

Manufacturing Procedure:
1. Lanthanum carbonate octahydrate was mixed with Intragranular excipients and sifted through sifter fitted with screen #30,
2. Blend of Step 1 was loaded in to RMG and mixed for 10 minutes.
3. Preparation of binder solution: Hydroxypropyl cellulose is added to purified water under continues stirring to get clear solution
4. The Step-2 is granulated using binder solution of step-3 in RMG to get required wet mass of powder blend
5. The wet mass of step 4 was sifted through sifter fitted with screen #16,
6. Wet granules are dried for sufficient period time to get LOD between 2 to 4% at 60° C.
7. Dried granules of step-6 is sifted through sifter fitted with screen #20,
8. The granules blend of Step-7 was blended with the extragranular ingredients in bin blender for 10 minutes.
9. Blend of step-8 is compressed using 24 mm round punches and corresponding dies.

EXAMPLE 7

| Sr. No | Ingredients | mg/Tablets |
|---|---|---|
| 1 | Lanthanum carbonate d (0.9) is 105 microns | 2166.3 |
| 2 | Avicel CE 15 | 88.67 |
| 3 | Hydroxypropyl cellulose | 30.0 |
| 4 | Acesulfame K | 30.0 |
| 5 | Microcrystalline Cellulose (Part I) | 173.208 |
| 6 | Microcrystalline Cellulose (Part II) | 259.812 |
| 7 | Colloidal Silicon dioxide | 32.01 |
| 8 | Magnesium Stearate | 20.0 |
| 9 | Purified Water | qs |
| | Tablet weight | 2800.00 |

Manufacturing Process:
1. All the ingredients were shifted through mechanical sifter fitted with suitable mesh size.
2. Ingredients like Lanthanum carbonate, Avicel CE 15, Acesulfame K, colloidal silicon dioxide and Microcrystalline cellulose (Part I) were loaded in to the Rapid mixture granulator and dry mixed for 10 minute under Impeller slow speed and chopper off.
3. Binder solution was prepared by dissolving HPC in purified water under continues stirring to get clear solution.
4. Step 2 was granulated using the binder solution of step 3 in to the Rapid mixture granulator for 10 minute under Impeller slow speed and chopper slow.
5. Wet granules were dried to achieved required LOD and milled using Quadra-co mill fitted with suitable mesh size
6. Granules of step 5 were blended with the magnesium stearate and microcrystalline cellulose (Part II) in bin blender for the period of 10 minutes.
7. Lubricated blend of step 6 was compressed using suitable tooling.

EXAMPLE 8

| Sr. No | Ingredients | mg/Tablets |
| --- | --- | --- |
| 1 | Lanthanum carbonate d (0.9) is 250 microns | 2140.037 |
| 2 | Avicel CE 15 | 88.67 |
| 3 | Hydroxypropyl cellulose | 42.0 |
| 4 | Acesulfame K | 30.0 |
| 5 | Colloidal Silicon dioxide | 32.0 |
| 6 | Microcrystalline Cellulose (Part I) | 122.0 |
| 7 | Microcrystalline Cellulose (Part II) | 325.0 |
| 8 | Magnesium Stearate | 20.0 |
| 9 | Purified Water | qs |
| | Tablet weight | 2799.7 |

Manufacturing Process:
1. All the ingredients were shifted through mechanical sifter fitted with suitable mesh size.
2. Ingredients like Lanthanum carbonate, Avicel CE 15, Acesulfame K, colloidal silicon dioxide and Microcrystalline cellulose (Part I) were loaded in to the Rapid mixture granulator and dry mixed for 10 minute under Impeller slow speed and chopper off.
3. Binder solution was prepared by dissolving HPC in purified water under continues stirring to get clear solution.
4. Step 2 was granulated using the binder solution of step 3 in to the Rapid mixture granulator for 10 minute under Impeller slow speed and chopper slow.
5. Wet granules were dried to achieved required LOD and milled using Quadra-co mill fitted with suitable mesh size
6. Granules of Step 5 were blended with the magnesium stearate and microcrystalline cellulose (Part II) in bin blender for the period of 10 minutes.
7. Lubricated blend of step 6 was compressed using suitable tooling.

EXAMPLE 9

| Sr. No | Ingredients | mg/Tablets |
| --- | --- | --- |
| 1 | Lanthanum carbonate d (0.9) - 105 microns | 2140.037 |
| 2 | Avicel CE 15 | 88.67 |
| 3 | Hydroxypropyl cellulose | 49 |
| 4 | Acesulfame K | 30.0 |
| 5 | Microcrystalline Cellulose (Part I) | 122.906 |
| 6 | Microcrystalline Cellulose (Part II) | 318.296 |
| 7 | Colloidal Silicon dioxide | 32.01 |
| 8 | Magnesium Stearate | 20.0 |
| 9 | Purified Water | qs |
| | Tablet weight | 2800.06 |

Manufacturing Process:
1. All the ingredients were shifted through mechanical sifter fitted with suitable mesh size.
2. Ingredients like Lanthanum carbonate, avicel CE 15, acesulfame K, colloidal silicon dioxide and microcrystalline cellulose (Part I) were loaded in to the Rapid mixture granulator and dry mixed for 10 minute under Impeller slow speed and chopper off.
3. Binder solution was prepared by dissolving hydroxypropyl cellulose in purified water under continues stirring to get clear solution.
4. Step 2 was granulated using the binder solution of step 3 in to the Rapid mixture granulator for 10 minute under Impeller slow speed and chopper slow.
5. Wet granules were dried to achieved required LOD and milled using Quadra-co mill fitted with suitable mesh size
6. Granules of step 5 were blended with the magnesium stearate and microcrystalline cellulose (Part II) in bin blender for the period of 10 minutes.
7. Lubricated blend of step 6 was compressed using suitable tooling.

EXAMPLE 10

| Sr. No | Ingredients | mg/Tablets |
| --- | --- | --- |
| 1 | Lanthanum carbonate d (0.9) - 250 microns | 2140.037 |
| 2 | Avicel CE 15 | 88.67 |
| 3 | Hydroxypropyl cellulose | 42.0 |
| 4 | Acesulfame K | 30.0 |
| 5 | Colloidal Silicon dioxide | 32.0 |
| 6 | Microcrystalline Cellulose (Part I) | 122.0 |
| 7 | Microcrystalline Cellulose (Part II) | 325.0 |
| 8 | Magnesium Stearate | 20.0 |
| 9 | Purified Water | qs |
| | Tablet weight | 2799.7 |

Manufacturing Process:
1. All the ingredients were shifted through mechanical sifter fitted with suitable mesh size.
2. Ingredients like Lanthanum carbonate, Avicel CE 15, Acesulfame K, colloidal silicon dioxide and Microcrystalline cellulose (Part I) were loaded in to the Rapid mixture granulator and dry mixed for 10 minute under Impeller slow speed and chopper off 3. Binder solution was prepared by dissolving HPC in purified water under continues stirring to get clear solution.
4. Step 2 was granulated using the binder solution of step 3 in to the Rapid mixture granulator for 10 minute under Impeller slow speed and chopper slow.
5. Wet granules were dried to achieved required LOD and milled using Quadra-co mill fitted with suitable mesh size
6. Granules of Step 5 were blended with the magnesium stearate and microcrystalline cellulose (Part II) in bin blender for the period of 10 minutes.
7. Lubricated blend of step 6 was compressed using suitable tooling.

Stability Studies:

Stability study of Lanthanum carbonate chewable tablets, 1000 mg was carried out in sealed HDPE container and this sealed HDPE containers were stored in accelerated stability condition at 40° C./75% relative humidity and XRD was performed on tablets withdrawn at specified internals of 1, 2 and 3 months. The XRD graphs are depicted in FIGS. 1 and 2, summarizing the stability test results of example 1 and example 4. No decarboxylation of Lanthanum carbonate was seen over the entire length of experiment and which is confirmed by the absence of Lanthanum hydroxycarbonate peak in the XRD graphs.

Phosphate Binding Study:

Fosrenol Tablets® Vs. Lanthanum Carbonate Octahydrate chewable tablets

Phosphate binding studies were done in 100 mM $(PO_4)^{-3}$ solution at room temperature.

Sample is weighed equivalent to 134 mg of elemental Lanthanum

After adding the sample in 50 ml of Phosphate ion solution shaken for 10 minutes and pH was adjusted by adding 0.1 N HCl or 1 N NaOH to the desired pH.

The slurry was shaken for two hours with the aid mechanical shaker and then filtered.

Then phosphate binding was estimated using making a complex with the reagents to yield graded color response depending upon the amount of $(PO_4)^{-3}$ present in the filtrate. (Reagents used were Ammonium Molybdate and Ascorbic acid)

Phosphate binding capacity (mmol/g) determined by calculating un-reacted phosphate in the solution.

TABLE 1

Results of the comparative Phosphate binding studies Example 1 and Fosrenol Tablets ®

| Batch No. | Phosphate binding Capacity (mmol/g) | | |
| --- | --- | --- | --- |
| | pH 3 | pH 4.3 | pH 7 |
| FOSRENOL Tablets ® | 7.7 | 7.4 | 8.5 |
| Example 5 | 7.9 | 8 | 8 |

Comparative Dissolution Study of Example 7 Vs. Example 9:

The dissolution test was carried out using modified USP III apparatus at 10 DPM, 900 ml of pH 0.25N HCl at 37±0.5° C.

Example 7: Formulation containing Lanthanum carbonate having particle size distribution d (0.9) about 105 microns Example 8: Formulation containing Lanthanum carbonate having particle size distribution d (0.9) about 250 microns

TABLE 2

Results of the comparative dissolution study of Example 7 and Example 8

| | Cumulative % Lanthanum carbonate Dissolved | |
| --- | --- | --- |
| Time (mins) | Average of Example 7 Lanthanum carbonate d(0.9) is 105 µm | Average of Example 8 Lanthanum carbonate d(0.9) is 250 µm |
| 10 | 0 | 0 |
| 15 | 38 | 20 |
| 20 | 56 | 42 |
| 30 | 70 | 61 |
| 45 | 85 | 78 |
| 60 | 95 | 92 |
| 90 | 100 | 100 |
| 120 | 102 | 101 |

Assessment of Lanthanum Carbonate Chewable Tablets for Chalkiness, Grittiness and Dryness:

The selected panel of 12 healthy human volunteers was requested to taste the chewable lanthanum carbonate tablets by keeping in the mouth till they disintegrated and rank it on a scale of perception ranging from 0-5.

Example 7: Formulation containing Lanthanum carbonate having particle size distribution d (0.9) about 105 micron.

Example 8: Formulation containing Lanthanum carbonate having particle size distribution d (0.9) about 250 micron.

Example 9: Formulation without lanthanum carbonate.

TABLE 3

Results of assessment of Lanthanum Carbonate Chewable Tablets for Chalkiness, Grittiness and Dryness

| Volunteers code | Formulations | | | | | | | | |
| --- | --- | --- | --- | --- | --- | --- | --- | --- | --- |
| | Example 7 | | | Example 8 | | | Example 9 (placebo) | | |
| | A | B | C | A | B | C | A | B | C |
| 1 | 2 | 2 | 2 | 3 | 3 | 3 | 1 | 1 | 1 |
| 2 | 1 | 3 | 2 | 3 | 3 | 3 | 1 | 1 | 1 |
| 3 | 2 | 3 | 2 | 3 | 2 | 3 | 1 | 2 | 1 |
| 4 | 2 | 1 | 2 | 2 | 1 | 3 | 2 | 1 | 1 |
| 5 | 2 | 1 | 1 | 2 | 2 | 4 | 1 | 2 | 2 |
| 6 | 3 | 2 | 1 | 3 | 2 | 2 | 1 | 2 | 1 |
| 7 | 1 | 2 | 1 | 3 | 3 | 2 | 1 | 2 | 1 |
| 8 | 2 | 1 | 1 | 4 | 3 | 3 | 1 | 2 | 2 |
| 9 | 2 | 2 | 3 | 3 | 3 | 3 | 2 | 1 | 1 |
| 10 | 2 | 2 | 2 | 4 | 3 | 3 | 1 | 1 | 2 |
| 11 | 1 | 2 | 2 | 3 | 4 | 2 | 1 | 1 | 1 |
| 12 | 2 | 2 | 1 | 3 | 3 | 3 | 2 | 2 | 2 |

Note:
A denotes Chalkiness, B denotes Grittiness and C denotes Dryness

We claim:

1. A stable wet granulated pharmaceutical composition in the form of a tablet for human use comprising:
    a) more than 70% weight by weight of lanthanum carbonate octahydrate; and
    b) a pharmaceutically acceptable diluent or carrier excluding monosaccharide(s) and disaccharide(s);
    wherein the composition does not exhibit decarboxylation of lanthanum carbonate after three months of storage at 40° C. and 75% humidity.

2. The composition according to claim 1, wherein said diluent or carrier is selected from the group consisting of microcrystalline cellulose, silicified microcrystalline cellulose, powdered cellulose and mixtures thereof.

3. The composition according to claim 1, wherein said lanthanum carbonate octahydrate has a particle size distribution such that the d (0.9) is not more than 110 microns.

4. The composition according to claim 1, wherein said composition further contains one or more pharmaceutically acceptable excipients selected from the group consisting of binders, disintegrants, sweeteners, flavors, surfactants, glidants, lubricants and mixtures thereof.

5. The composition according claim 4, wherein said binder is selected from a group consisting of methyl cellulose, ethyl cellulose, hydroxypropyl cellulose, hydroxypropyl methylcellulose, sodium carboxymethyl cellulose, gelatin, polyvinylpyrrolidone, poly(meth)acrylates, and mixtures thereof.

6. A process for preparing a wet granulated lanthanum carbonate composition in the form of a stable tablet containing more than 70% w/w of lanthanum carbonate octahydrate, wherein said process comprises the steps of:
   a) blending lanthanum carbonate octahydrate, with at least one diluent or carrier and optionally other pharmaceutically acceptable excipients to form a blend;
   b) granulating the blend of step (a) with a binder solution to foam granules;
   c) optionally, blending the granules of step (b) with one or more lubricants, and/or one or more extra granular ingredients to get a final blend; and
   d) compressing said final blend to form tablets; wherein said diluent or carrier excludes monosaccharides and disaccharides and wherein the composition does not exhibit decarboxylation of lanthanum carbonate after three months of storage at 40° C. and 75% humidity.

7. The process according to claim 6, wherein said binder solution comprises at least one binder dissolved/dispersed in a granulating fluid.

8. The process according to claim 6, wherein said diluent or carrier is selected from the group consisting of microcrystalline cellulose, silicified microcrystalline cellulose, powdered cellulose and mixtures thereof.

9. The process according to claim 6, wherein said lanthanum carbonate octahydrate has a particle size distribution such that the d (0.9) is not more than 110 microns.

10. The process according to claim 7, wherein said binder is selected from a group consisting of methyl cellulose, ethyl cellulose, hydroxypropyl cellulose, hydroxypropyl methylcellulose, sodium carboxymethyl cellulose, gelatin, polyvinylpyrrolidone, poly(meth)acrylates, and mixtures thereof.

11. The process according to claim 6, wherein said composition optionally contains one or more pharmaceutically acceptable excipients selected from the group consisting of disintegrants, sweeteners, flavors, surfactants, glidants, and mixtures thereof.

12. A stable wet granulated lanthanum carbonate composition in the form of a tablet comprising more than 70% w/w of lanthanum carbonates octahydrate, 5 to 25% w/w of microcrystalline cellulose, 0 to 5% w/w of hydroxypropyl cellulose and 0 to 10% w/w of powdered cellulose, wherein the composition excludes monosaccharides and disaccharides, and wherein the composition does not exhibit decarboxylation of lanthanum carbonate after three months storage at 40° C. and 75% humidity.

13. The composition according to claim 12, wherein said composition comprises more than 70% w/w of lanthanum carbonates octahydrate, from about 8 to about 15% w/w of microcrystalline cellulose, from about 1 to about 3% w/w of hydroxypropyl cellulose and 0 to about 10% w/w of powdered cellulose.

14. The composition according to claim 13, wherein said composition further comprises from about 0.5 to about 1.5% w/w of acesulfame potassium and from about 2 to about 4% of Avicel CE15.

* * * * *